(12) United States Patent
Pelletier et al.

(10) Patent No.: US 10,064,083 B2
(45) Date of Patent: Aug. 28, 2018

(54) UNIVERSAL COMMUNICATION SYSTEM FOR MEASUREMENT APPARATUSES, METHOD OF COMMUNICATION RELATING THERETO

(71) Applicant: ECOMESURE, Saclay (FR)

(72) Inventors: Damien Pelletier, Orsay (FR); Cédric Neveu, Montrouge (FR); Fabio Furlan, Saint-Michel-sur-Orge (FR)

(73) Assignee: ECOMESURE, Saclay (FR)

( * ) Notice: Subject to any disclaimer, the term of this patent is extended or adjusted under 35 U.S.C. 154(b) by 0 days.

(21) Appl. No.: 15/560,457

(22) PCT Filed: Mar. 24, 2016

(86) PCT No.: PCT/EP2016/056602
§ 371 (c)(1),
(2) Date: Sep. 21, 2017

(87) PCT Pub. No.: WO2016/151096
PCT Pub. Date: Sep. 29, 2016

(65) Prior Publication Data
US 2018/0077593 A1    Mar. 15, 2018

(30) Foreign Application Priority Data

Mar. 25, 2015 (FR) ...................................... 1552497

(51) Int. Cl.
*H04W 24/10* (2009.01)
*H04W 76/02* (2009.01)
(Continued)

(52) U.S. Cl.
CPC ........ *H04W 24/10* (2013.01); *G01N 33/0075* (2013.01); *H04L 67/12* (2013.01);
(Continued)

(58) Field of Classification Search
CPC .................. H04L 12/2838; H04L 12/2803
See application file for complete search history.

(56) References Cited

U.S. PATENT DOCUMENTS

| 2003/0187920 | A1 | 10/2003 | Redkar |
| 2010/0306547 | A1* | 12/2010 | Fallows ................ G06F 21/305 713/178 |

(Continued)

OTHER PUBLICATIONS

French Search Report from French Patent Application No. 1552497, dated Jan. 14, 2016.
(Continued)

*Primary Examiner* — Arvin Eskandarnia
(74) *Attorney, Agent, or Firm* — Greer, Burns & Crain, Ltd.

(57) ABSTRACT

A universal communication system for measurement apparatuses is provided, including:
  a remote server having:
  a data storage location,
  a remote platform of the lightweight client type configured so as to interact with at least part of a plurality of measurement instruments;
  at least one gateway disposed between the remote server and the plurality of measurement instruments, the at least one gateway including:
    first bidirectional connector with the plurality of measurement instruments;
    second bidirectional connector with the remote server; and
    a processing unit configured to communicate with the measurement instruments according to a plurality of communication protocols, the processing unit being devised so as to store and execute at least one software application.

10 Claims, 2 Drawing Sheets

(51) Int. Cl.
　　　G01N 33/00　　　(2006.01)
　　　H04L 29/08　　　(2006.01)
　　　H04W 84/12　　　(2009.01)
　　　H04W 76/19　　　(2018.01)
(52) U.S. Cl.
　　　CPC ......... *H04W 76/028* (2013.01); *H04W 76/19* (2018.02); *H04W 84/12* (2013.01)

(56) References Cited

U.S. PATENT DOCUMENTS

| | | |
|---|---|---|
| 2011/0202189 A1 | 8/2011 | Venkatakrishnan et al. |
| 2012/0105249 A1* | 5/2012 | Bauerfeld ......... H04L 29/12301 340/870.02 |
| 2013/0046412 A1* | 2/2013 | Chan ..................... G01D 4/004 700/286 |
| 2013/0282196 A1 | 10/2013 | Tappeiner |

OTHER PUBLICATIONS

International Search Report from International Patent Application No. PCT/EP2016/056602, dated Jun. 16, 2016.
Written Opinion from International Patent Application No. PCT/EP2016/056602, dated Jun. 16, 2016.

\* cited by examiner

UNIVERSAL COMMUNICATION SYSTEM FOR MEASUREMENT APPARATUSES, METHOD OF COMMUNICATION RELATING THERETO

BACKGROUND

The present invention relates to a universal communication system for measurement instruments.

The present invention concerns the field of the networking of measurement instruments.

In the particular field of the metrology of aerosols and air quality, devices for measuring air quality and the presence of aerosols in the air are very widespread over urban areas. Thus, a very large number of measurement devices exist making it possible to measure numerous parameters relating to air quality and to the aerosols present, in order to determine in particular pollution levels and warning thresholds.

Large numbers of actors offer measurement devices incorporating sensors the technologies of which are varied and the communication protocols sometimes specific. Thus it is very difficult to gather together all of the data measured by these different measurement devices within one and the same computer network.

Solutions for interconnecting these measurement devices using computers equipped with communication cards, storage means and complex software incorporating all of the protocols for communication with said measurement devices are known. These solutions are called "fat client" as all of the software and communication protocols are incorporated on said computers which are connected to the measurement devices. It is thus necessary to associate each measurement instrument with a computer, and the communication software and protocols must be adapted to each measurement instrument.

The drawbacks associated with the current solutions are the high cost of the infrastructure required (each measurement instrument being associated with a computer), and a level of reliability limited by the hardware architecture. Furthermore, the addition of a new sensor that is not managed requires a local update on each station connected to the measurement devices. Finally, these solutions require a high level of maintenance, in particular because of the computer interface, the software architecture and the updating thereof.

In the wider fields of scientific instrumentation (measurements of water quality, levels of noise, traffic, odours, seismic measurements, meteorological measurements etc.) and the networking of measurement instruments which have been relocated and do not incorporate sufficient telecommunication means, the problems mentioned above remain valid.

A subject of the present invention is to respond at least in large part to the aforementioned problems and moreover to lead to other advantages.

Another purpose of the invention is to solve at least one of these problems by a novel communication system between measurement devices, in particular in the field of the metrology of aerosols and of air quality.

Another purpose of the present invention is to reduce the costs and the maintenance associated with the network architecture of such measurement devices.

Another purpose of the present invention is to improve the reliability of such a network architecture.

Another purpose of the invention is to improve the accessibility of the data measured by the measurement devices, and in particular those in the field of the metrology of aerosols and of air quality.

SUMMARY

According to a first aspect of the invention, at least one of the aforementioned objectives is achieved with a universal communication system for measurement devices, in particular those dedicated to the metrology of air quality and of aerosols, said system comprising (i) a remote server comprising storage means and a remote platform of the thin client type, configured in order to interact with at least one part of a plurality of measurement instruments and (ii) at least one gateway arranged between the remote server and the plurality of measurement instruments, said at least one gateway comprising:

first means for bidirectional connection with the plurality of measurement instruments,
second means for bidirectional connection with the remote server,
a processing unit configured in order to communicate with said measurement instruments according to a plurality of communication protocols, said processing unit being arranged in order to store and execute at least one software application.

The present invention relates particularly—but not exclusively—to the networking and the communication between instruments for measuring air quality and aerosols. However, other fields of use are addressed by the present invention, in particular that of measurements of water quality, levels of noise, traffic, odours, seismic or radioactive measurements, meteorological measurements (temperature, pressure, hygrometry etc.)

It is thus possible to network a plurality of measurement instruments using a low-cost system: the software and hardware architecture is concentrated at a communication node which is arranged and configured in order to communicate—downstream—with any measurement instrument thanks to numerous different communications means, making it possible to adapt to very many types of measurement instruments and communication protocols; and—upstream—with any client having an internet connection. The reliability of the novel solution proposed by the present invention is also more reliable than the solutions known up to now.

Maintenance is thus facilitated as it is sufficient to intervene in a single place in order to repair any faults. Thanks to a remote connection, it is also possible to update the software infrastructure so as for example to be able to communicate with new measurement instruments and/or according to new communication protocols.

Finally, thanks to the internet connection and to the remote server, it will be possible from now on to access a very large amount of information relating to the measurement instruments from any location, without having to travel in order to download the data recorded by a particular measurement instrument (and/or somewhat out of date, without modern communications means etc.), without needing to use a particular software, and in a centralized way; a system according to the invention making it possible to address a plurality of measurement instruments. The accessibility of the data measured—inter alia—is therefore improved.

The system according to the invention thus comprises two fundamental aspects: a downstream communication to the measurement instruments and an upstream communication via the internet to make available a certain amount of data relating to the measurement instruments.

The downstream communication between the gateway and the measurement instruments makes it possible to transport the data relating to each measurement instrument without interpreting the content. It is a bidirectional communication and said data can be of any type. By way of non limitative example, it can be data relating to physical measurements carried out by said measurement instruments, configuration parameters of said measurement instruments then transmitted via the gateway to the measurement instrument, software updates of said measurement instruments etc.

The gateway comprises a hardware and software architecture making it possible to act as a local web server. It can moreover comprise the very latest data flow connectivity and security technologies (Firewall, SSL, SSH, etc.).

Preferably, the communication system according to the invention uses robust industrial technologies and storage means of the flash memory type rather than a rotating hard disk. The processing unit can be of any known type, such as for example microprocessor; microcontroller etc. generally, the gateway comprises software and hardware reserve capacity which makes it possible to change and adapt to the specific needs of the measurement instruments and to incorporate possible future additional modules.

The upstream communication to the internet complements the downstream communication and makes it possible to establish a physical and software interconnection between any type of measurement instrument via the gateway and the remote server according to a very large number of communication means without the addition of software and/or a communication protocol.

The remote server is configured in order to store all the data relating to the measurement instruments included in the network formed by the system according to the invention.

Preferably, it can comprise all the known technologies for securing the storage and the access to said stored data. By way of non limitative examples, the access to the server can be secured by an access with an identifier and password; the recorded data can be encrypted.

The remote server also comprises a remote platform accessible in Software As A Service (SAAS) mode.

The platform is of the thin client type, i.e. that it is accessible from a simple internet browser on any computer support (tablet, computer, smartphone etc.) without the installation of specific software.

Preferably, the remote platform architecture is designed based on known technologies for high-traffic web platforms. It is also configured in order to be replicated at any time for backups, transfers, upgrades to the processing unit, in particular by the addition of memory units.

Advantageously, the remote platform is configured in order to partition the stored data in order to reinforce security.

The remote platform constitutes the intelligence of the system according to the invention and, in particular, it comprises the protocols for communication with the measurement devices. If necessary, new communication protocols can be added to the platform via the internet.

It is thus possible to have access from the remote platform to a very large amount of data relating to the instruments, but also specifically to set the parameters thereof. By way of non limitative examples, the remote platform makes it possible in particular to display in real time the status of the measurement instruments and of the measurements carried out, to display and download the data relating to each instrument and/or the corresponding history, to define operational warnings and/or those for exceeding certain thresholds, the parameters of which can be set, to edit and download summary reports relating to each instrument, to take remote control, to carry out remote maintenance, to control inputs/outputs and/or to carry out automated ftp transfers.

The remote server is moreover configured in order to allow the user to add new functionalities or new measurement devices directly from the remote server, which allows centralized updating for all the clients of the remote platform and therefore reduced usage and maintenance costs.

Advantageously, in a universal communication system according to the first aspect of the invention, the first connection means can be of the Ethernet and/or RS232 and/or USB and/or wireless type. The processing unit comprised in the gateway is configured in order to store the protocols for communication with the measurement instruments and relating to said first communication means.

Preferably, in a universal communication system according to the first aspect of the invention, the second connection means can be of the wired or wireless type. By way of non limitative examples, the methods of connection with the remote network—and therefore to the internet—can be of the Ethernet or Wifi type, or according to any of the telecommunication standards: GPRS, 2G, 3G, 4G etc.

Advantageously, in a universal communication system according to any one of the embodiments of the first aspect of the invention, the data sent to the remote server can be encapsulated and/or encrypted.

Generally, a particular communication protocol is defined between the gateway and the remote server, allowing the exchange and the encapsulation of the data without interpreting the content. The particular communication protocol thus provides a container for the transport of the data exchanged between the gateways and the remote server. Moreover, it also ensures the deencapsulation of the data and protocols transferred from the remote server to the measurement instruments. Encapsulation and deencapsulation are carried out both by each gateway and by the remote platform.

The last remote server understands the addressing commands of the local measurement instruments. The addressing commands pass through the internet layers in order to arrive at a gateway which then transfers said commands to the measurement instruments concerned.

Thus, the encapsulation protocol comprises on the one hand the internet address of the gateway through which the information must be conveyed, and on the other hand the link between the measurement instrument and said gateway by which they are connected.

In the down direction (remote server to measurement instrument), the encapsulated command is received by the gateway which deencapsulates said command without interpreting it and transfers it directly to the measurement instrument via the designated link.

In the up direction (measurement instrument to remote server), the instrument replies to the command to the gateway, which encapsulates the reply in order to send it to the remote platform which is, preferentially, the only one capable of interpreting the data contained in the reply.

Advantageously, the communication protocol between the remote server and the gateways is secure and encrypted according to the known civil encryption technologies.

Preferably, several gateways can be interconnected to the remote server in an encrypted and secure fashion and according to a known tunnelling technique.

Preferentially, the particular communication protocol of the present invention comprises additional functions, configured in order to monitor and control each gateway of the network thus formed.

Advantageously, the data transiting between the gateways and the remote server are not stored locally but on the remote server in order to benefit from the computer security functions and to allow permanent access to the data without having to re-poll the local measurement instruments.

Optionally, each gateway comprises storage means configured in order to temporarily record data from the measurement instruments. This temporary local storage thus allows any internet outages to be managed, and data from the measurement instruments to be recorded during this outage. When the connection is re-established, the data are transferred to the remote server.

According to a preferred embodiment according to any one of the embodiments of the first aspect of the invention, the remote platform can moreover be configured in order to directly control at least one measurement instrument remotely, preferentially by a thin client of the virtual window type emulating the control interface of said at least one measurement instrument. To this end, the remote server and/or the remote platform store all the communication protocols specific to each measurement instrument in order to be able to communicate with them and exchange data.

In fact, in the case where the measurement instrument comprises software commands allowing it to be controlled, the remote platform is configured in order to drive said measurement instrument remotely and to upload the data to the remote server and via a standardized user interface. In the case where the measurement instrument does not comprise commands allowing it to be controlled, a system is implemented to take control of the graphical interface of the measurement instrument in order to have the control window of the device on the internet platform without adding software on the client station. This particular graphical interface is developed at the time such a measurement instrument is incorporated into the network formed by the present invention.

Optionally, in a universal communication system according to any one of the embodiments of the first aspect of the invention, at least one gateway can comprise a manual or automatic geolocation means. It is thus possible to carry out statistical processing on sub-assemblies of measurement devices and to establish particular correlations between the data measured on the one hand and the location of the measurement instruments on the other hand. These correlations are very important in the particular field of air quality metrology. For measurement instruments that do not have internal geolocation means, the geolocation of the gateway can be a sufficient means for performing such correlations.

If the measurement instrument comprises internal geolocation means, then the geolocation information is automatically transferred via the gateway to the remote server and/or the remote platform. On the other hand, if the measurement instrument does not comprise internal geolocation means, then the geolocation information is recorded manually in the remote server and/or in the remote platform, for example when said measurement instrument is added to said system according to the invention.

According to another embodiment of the invention, according to any of the embodiments of the first aspect of the invention comprising a plurality of gateways, at least one first part of the plurality of gateways can be arranged in order to communicate with the remote platform, and at least one second part of the plurality of gateways can be connected to at least one gateway of said first part by the first connection means.

By way of non limitative example, each gateway can be configured in order to connect to another gateway within a local network, by wired or wireless (radio) communication means. This advantageous configuration thus makes it possible to define a communication subnetwork to measurement instruments, for example in areas which are difficult to access and/or outside any telecommunication network. This subnetwork can then advantageously be completed by a gateway which is connected both to this subnetwork (by the local communication means) and to the internet (by the remote communication means). It is thus possible to relay the data from the measurement devices of said subnetwork to the internet, and more particularly to the remote server in order to make said data accessible.

According to a second aspect of the invention, a method is proposed for the transfer of data from measurement instruments, said method implementing the system according to embodiments of the first aspect of the invention, said method comprising at least one iteration of the following steps:

transfer of the data from a measurement instrument to the gateway, via the first connection means, encapsulation of said measurement data by said gateway, transfer of the encapsulated data to the remote server using the second connection means.

Optionally, the encapsulation can comprise a step of encrypting the data. Moreover the transfer of the encapsulated data can be done, as described previously, according to known secure communication protocols.

Advantageously, the data transfer method according to the second aspect of the invention can comprise a step of parametering at least one measurement instrument by remote access:

displaying a graphical interface of the web client type configured in order to define the parametering variables of said instrument, transfer of said parametering variables to the gateway by the second connection means and via a secure transfer protocol, transfer of said parametering variables to said measurement instrument by the first connection means.

Optionally, the parametering of the at least one measurement instrument can be done by remote control and/or through a virtual window, as described previously.

Preferentially, the method according to any one of the versions of the second aspect of the invention can comprise a step of downloading a measurement protocol, arranged in order to communicate with at least one measurement instrument, onto the remote platform.

Advantageously, the protocols are stored on the remote platform exclusively. However, in the case of an internet outage, a command specific to each measurement instrument, defined by the remote platform and stored beforehand on the gateway when executed allows on the one hand, data originating from said measurement instruments to be stored for the duration of the outage, and on the other hand to be restored to the remote platform once the internet connection is re-established.

In particular, the system according to the invention can comprise:

a remote server comprising:

storage means, a remote platform of the thin client type and configured in order to interact with at least one part of a plurality of measurement instruments, at least one gateway arranged between the remote server and the plurality of measurement instruments, said at least one gateway comprising:

first means for bidirectional connection with the plurality of measurement instruments, second means for bidirectional connection with the remote server, a processing unit configured in order to communicate with said measurement instruments according to a plurality of communication protocols, said processing unit being arranged in order to store and execute at least one software application.

According to the invention, the protocols for communication with the measurement devices are exclusively stored on the remote platform. Moreover, the processing unit is configured in order to store in the gateway a command specific to each measurement instrument and defined by the remote platform, this command allowing in the case of an internet outage, data originating from said measurement instruments on the one hand to be stored for the duration of the outage, and on the other hand to be restored to the remote platform once the internet connection is re-established.

According to an advantageous embodiment of the invention, each communication protocol for all or part of the measurement devices comprises on the one hand presentation and application layers, such as for example all or part of the host layers in the OSI model, and on the other hand physical and link layers, such as for example the hardware layers in the OSI model. The presentation and application layers can comprise the syntax and semantics of the measurement instruments such as for example in the Modbus protocol, the AK protocol or proprietary protocols.

In addition to the above, according to the invention, the platform can be configured in order to communicate with the measurement instruments according to a plurality of communication protocols at the level of the presentation and application layers. Moreover, the processing unit of the gateway can communicate with the measurement devices according to a plurality of communication protocols at the level of the physical and data link layers.

Otherwise, each measurement instrument can be equipped with a dedicated software application in order to exploit the raw data originating from internal sensors of this instrument. According to the invention, this dedicated software application can be exclusively stored in the remote server and not on the gateway which then only acts to transfer raw data originating from internal sensors of the instrument, without capability for the exploitation thereof. For each device, this application can be a dedicated graphical user interface.

The commands of the devices originate directly from the remote server without interpretation by the gateway. In this case, the invention is particularly advantageous, as for each measurement device the protocol (for example ideally the entire protocol, not just the higher layers) for communication with this device is installed in the remote server and not in the gateway. The latter contains only the hardware layers allowing contact to be made with the device. The data are recovered and interpreted within the remote server and not in the gateway. The intelligence is located in the remote server. The gateway only recovers the frames originating from the device and transfers them to the remote server without reading the data. With such a transparent gateway, the remote server can easily access a set of measurement devices without parametering of the gateway, as only the remote server incorporates all of the protocols. The link between the remote server and the gateway is a pipe making it possible to pass the commands originating from the server to the devices.

In other words, the system according to the invention can comprise:

a remote server comprising:
storage means,
a remote platform of the thin client type and configured in order to interact with at least one part of a plurality of measurement instruments, at least one gateway arranged between the remote server and the plurality of measurement instruments, said at least one gateway comprising:

first means for bidirectional connection with the plurality of measurement instruments, second means for bidirectional connection with the remote server, a processing unit configured in order to communicate with said measurement instruments according to a plurality of communication protocols, said processing unit being arranged in order to store and execute at least one software application.

According to the invention, the protocols for communication with the measurement devices are exclusively stored on the remote platform, the server being configured in order to generate commands at the level of the higher layers of the protocols for communication with the devices, and the gateway being configured in order to communicate with the devices only at the level of the hardware layers of the protocols for communication with the devices. Moreover, the processing unit is configured in order to temporarily store in the gateway a command specific to each measurement instrument and defined by the remote platform, this command making it possible to in the case of an internet outage on the one hand to store the data originating from said measurement instruments for the duration of the outage and on the other hand to restore the data to the remote platform once the internet connection is re-established.

In fact, the gateway is configured in order to temporarily record commands originating from the remote server and to use them in case of an outage. By temporary, is meant for example a period during which the remote server is in communication with a device, this duration can be extended by the period linked to the outage.

BRIEF DESCRIPTION OF THE DRAWINGS

Other advantages and characteristics of the invention will become more apparent through the description which follows on the one hand, and several embodiments given non limitatively by way of indication, with reference to the attached diagrammatic drawings on the other hand, in which.

DETAILED DESCRIPTION

The embodiments which will be described below are in no way limitative; it is possible in particular to imagine variants of the invention comprising only a selection of characteristics described below in isolation from the other characteristics described, if this selection of characteristics is sufficient to confer a technical advantage or to differentiate the invention with respect to the state of the prior art. This selection comprises at least one, preferably functional, characteristic without structural details, or with only a part of the structural details if this part alone is sufficient to confer a technical advantage or to differentiate the invention with respect to the state of the prior art.

In particular, all the variants and all the embodiments described can be combined together if there is no objection to this combination from a technical point of view.

In the figures, the elements common to several figures retain the same reference.

Figure 1:
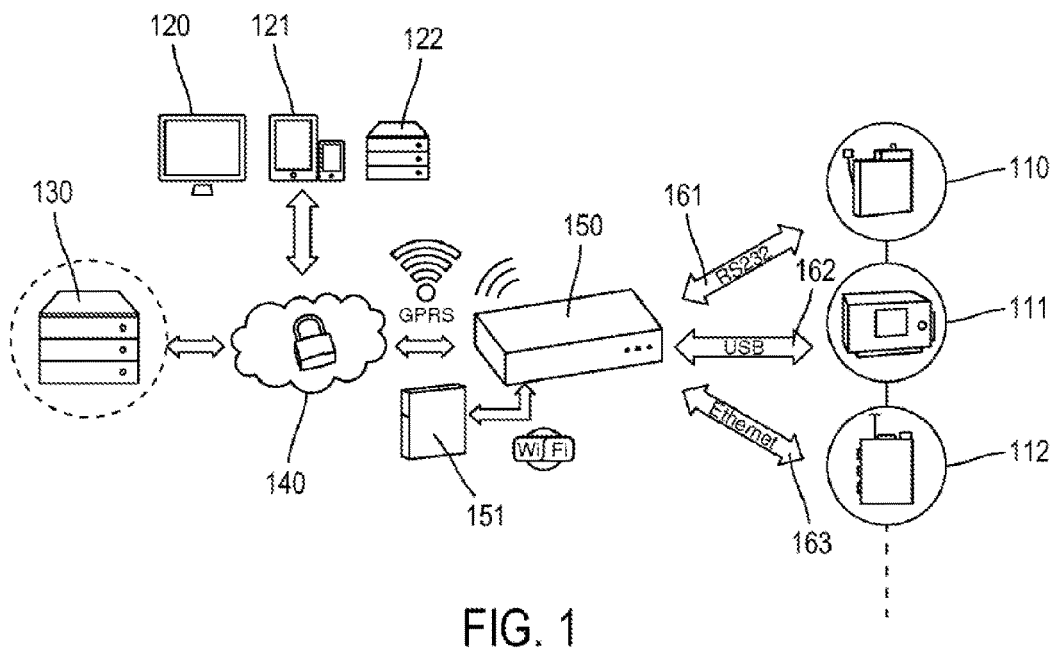
FIG. 1 shows a universal communication system for measurement instruments.

FIG. 1 describes a universal communication system for measurement instruments, in particular instruments for measuring air quality, and in which a plurality of measurement instruments 110-112 are connected to a gateway 150 via local connections of the RS232, USB, Ethernet type etc. The gateway 150 thus comprises first communication means 161-163 that are bidirectional and compatible with the plurality of measurement instruments.

The gateway comprises second bidirectional connection means 151, 152 arranged and configured in order to allow said gateway 150 to connect to the internet.

The connection to the internet 140 is advantageously carried out by secure means.

A remote server 130 comprising storage means and a remote platform (not shown) therefore makes available to clients 120-122 the measurement data sent by said measurement instruments 110-112 via the gateway 150. As described previously, the remote platform is configured in order to allow remote control and/or parametering of the measurement instruments 110-112.

The clients also access the remote server 130 securely 140, using a simple web browser, without any particular software application. Thus, access to the remote server 130 and to the platform is possible from a computer 120, a smartphone or a tablet 121 or an ftp server 122, internet API platforms etc.

Figure 2:
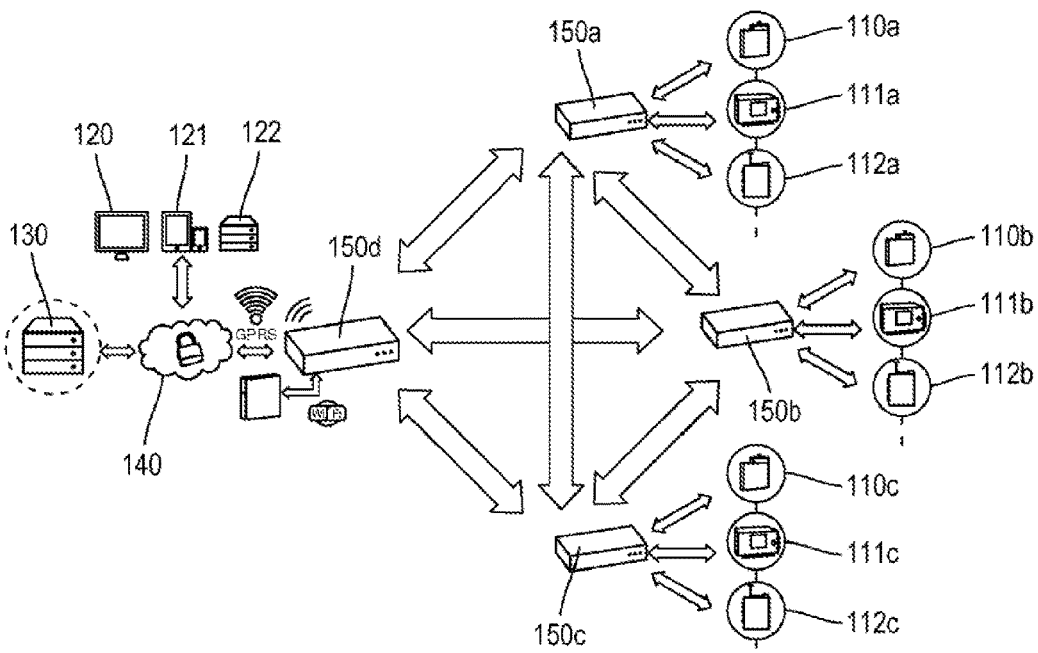
FIG. 2 shows a particular network architecture of the universal communication system according to the invention.

FIG. 2 shows a particular network architecture of the universal communication system according to the invention, in which a local subnetwork grouping several instrument groups is interfaced by a gateway, which itself has internet access.

Each gateway 150a, 150b, 150c of the subnetwork interface thus has plurality of measurement instruments, 110a, 111a, 112a, 110b, 111b, 112b and 110c, 111c, 112c respectively.

Each gateway 150a, 150b, 150c communicates with all the others 150a, 150b, 150c through a local network and via the first communication means.

In addition, each gateway 150a, 150b, 150c also communicates with the gateway 150d by the first communication means.

The gateway 150d is arranged and configured on the one hand in order to communicate with the gateways 150a, 150b, 150c of the sub-network by local communication means, and on the other hand in order to communicate via the internet and remote second communication means.

The gateway 150d thus makes it possible to communicate with the remote server 130 via a secure access 140, and thus allows all the gateways of the subnetwork to communicate, via it, with the internet through the gateway and to have access to the remote server. Thus, all of the measurement instruments of the subnetwork which, at the start, were not connected to the internet, can thanks to this network architecture be connected to the remote server, to the remote platform, and benefit from all of the functionalities of the present invention.

Figure 3:
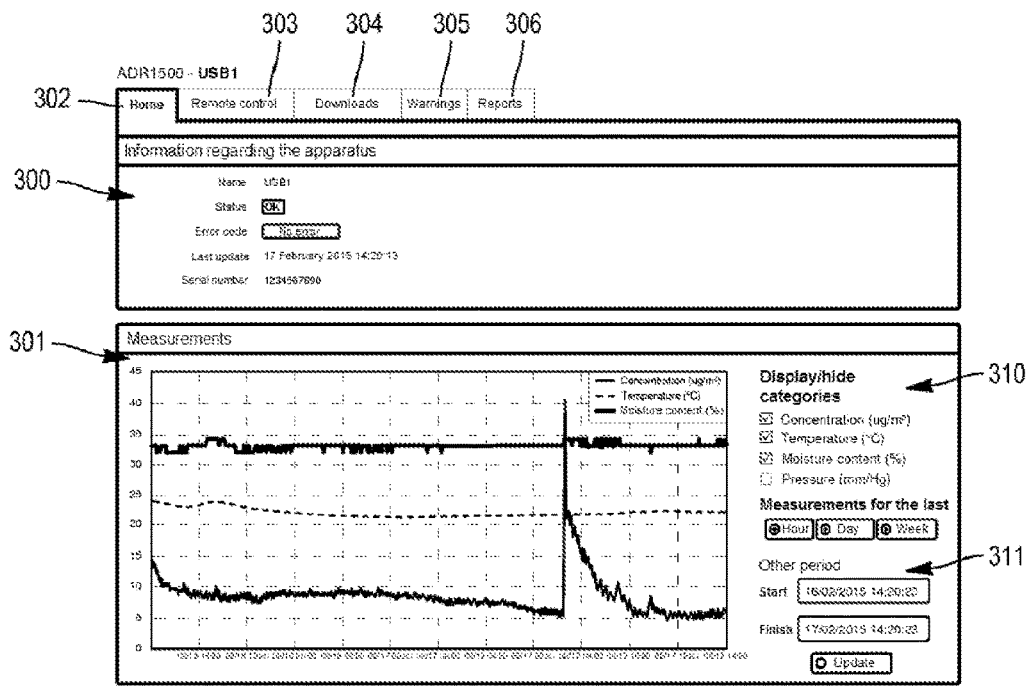
FIG. 3 shows a view of the remote platform representing the measurements carried out by a measurement instrument.

FIG. 3 shows a view of the remote platform representing the measurements carried out by a measurement instrument.

Several tabs 302-306 make it possible to select different display functionalities on the web client: the remote control 303 of the measurement instrument, the downloading 304 of the measurements carried out, the definition of warnings 305 and the generation of reports 306.

The home tab 302 is the one that is active in FIG. 3. It foregrounds a first frame 300 relating to the information of the measurement instrument the data of which are displayed on the screen (the name, status thereof, an error code, a serial number and the date the data were updated).

A second frame 301 displays a graph representing the measurement data for a given period.

Two control areas 310 and 311 make it possible to respectively select the curves to be displayed on the graph and to select the period of time to be displayed.

Figure 4:
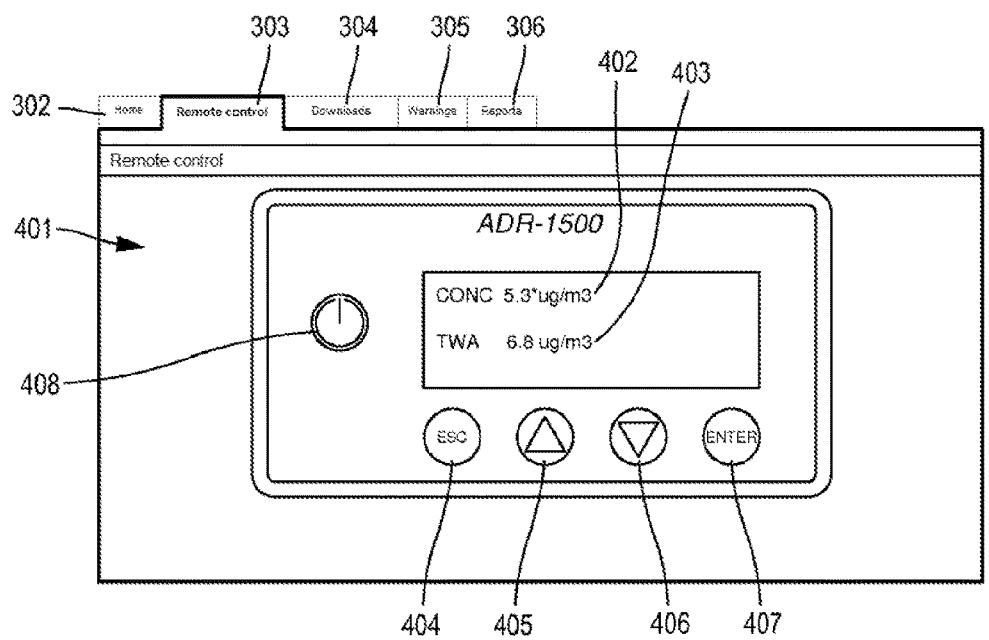
FIG. 4 shows a virtual window for the remote control of a measurement instrument.

FIG. 4 shows a virtual window for the remote control of a measurement instrument with a software interface. This interface is represented in the "Remote control" tab 303, and more particularly within a frame 401.

A user interface reproducing the graphical interface of the software of the measurement instrument which is controlled via the remote platform is displayed by said remote platform. The graphical interface represents the front face of the measurement instrument, with a series of buttons 404-408 making it possible respectively to leave a menu, increment a numerical value, decrement a numerical value, validate a value and turn off the measurement instrument.

On the screen simulated by the graphical interface, two parameters 402 and 403 are configurable. Modification of the values of each parameter, once validated, will be transmitted to the measurement instrument via the network and via the communication protocol of the universal communication system on the one hand, via the communication protocol of the measurement instrument on the other hand, and via the gateway.

Of course, the invention is not limited to the examples which have just been described and numerous adjustments can be made to these examples without exceeding the scope of the invention. In particular, the various characteristics, forms, variants and embodiments of the invention can be combined together in various combinations provided that they are not incompatible or mutually exclusive. In particular, all the previously described variants and embodiments can be combined together.

The invention claimed is:

1. A universal communication system for measurement devices, said system comprising:
   a remote server comprising:
   storage means;
   a remote platform of the thin client type, configured in interact with at least one part of a plurality of measurement instruments;
   at least one gateway arranged between the remote server and the plurality of measurement instruments, said at least one gateway comprising:
   first means for bidirectional connection with the plurality of measurement instruments;
   second means for bidirectional connection with the remote server;
   a processing unit configured to communicate with said measurement instruments according to a plurality of communication protocols, said processing unit being arranged to store and execute at least one software application;

the protocols for communication with the measurement devices are exclusively stored on the remote platform; and the processing unit is configured to store in the gateway a command specific to each measurement instrument and defined by the remote platform, this command making it possible in the case of an internet outage to store data originating from said measurement instruments for the duration of the outage and furthermore to restore the data to the remote platform once the internet connection is re-established.

2. The system according to claim 1, characterized in that the first connection means are of the Ethernet and/or RS232 and/or USB and/or wireless type, and/or the second connection means are of the wired and/or wireless type.

3. The system according to claim 1, characterized in that the data sent to the remote server are encapsulated and/or encrypted.

4. The system according to claim 1, characterized in that the remote platform is moreover configured to directly remotely control distance at least one measurement instrument.

5. The system according to claim 4, characterized in that the remote control is carried out by a thin client of the virtual window type emulating the control interface of said at least one measurement instrument.

6. The system according to claim 1, characterized in that at least one gateway comprises a manual or automatic geolocation means.

7. The system according to claim 1 and comprising a plurality of gateways, said system being characterized in that at least one first part of the plurality of gateways is arranged to communicate with the remote platform, and in that at least one second part of the plurality of gateways is connected to at least one gateway of said first part by the first connection means.

8. A method for the transfer of data from measurement instruments, said method implementing the system according to claim 3 and comprising at least one iteration of the following steps:
providing a universal communication system, comprising:
a remote server comprising:
storage means;
a remote platform of the thin client type, configured to interact with at least one part of a plurality of measurement instruments;
at least one gateway arranged between the remote server and the plurality of measurement instruments, said at least one gateway comprising:
first means for bidirectional connection with the plurality of measurement instruments;
second means for bidirectional connection with the remote server;
a processing unit configured to communicate with said measurement instruments according to a plurality of communication protocols, said processing unit being arranged to store and execute at least one software application;
the protocols for communication with the measurement devices are exclusively stored on the remote platform;
communication between the remote server and the communication devices by communication means protocols stored exclusively in the remote platform;
transfer of data from a measurement instrument to the gateway, via the first connection means;
encapsulation of said measurement data by said gateway;
transfer of the encapsulated data to the remote server using the second connection means; and
in case of an internet outage, a command specific to each measurement instrument, defined by the remote platform and stored beforehand on the gateway is used, when executed, to store data originating from said measurement instruments for the duration of the outage and furthermore to restore the data to the remote platform once the internet connection is re-established.

9. The method according to claim 8, further comprising a step of parametering at least one measurement instrument by remote access:
displaying a graphical interface of web client type configured to define the parametering variables of said instrument;
transfer of said parametering variables to the gateway by the second connection means and via a secure transfer protocol; and
transfer of said parametering variables to said measurement instrument by the first connection means.

10. The method according to claim 8, further comprising a step of downloading a measurement protocol, arranged to communicate with at least one measurement instrument, onto the remote platform.

* * * * *